United States Patent [19]
Blonder et al.

[11] Patent Number: 5,979,643
[45] Date of Patent: Nov. 9, 1999

[54] DENTAL IMPLANT PROSTHESIS COMPONENT DISPLAY SYSTEM

[75] Inventors: Howard Blonder, Downey; Gregory T. Anascavage, Irvine; Gregory M. Smith, Yorba Linda, all of Calif.

[73] Assignee: Nobel BioCare USA, Inc., Yorba Linda, Calif.

[21] Appl. No.: 08/926,302

[22] Filed: Sep. 5, 1997

[51] Int. Cl.⁶ ..................................................... A61B 19/02
[52] U.S. Cl. ..................... 206/63.5; 206/368; 206/459.5; 206/564
[58] Field of Search .................................. 206/63.5, 438, 206/459.5, 368, 369, 362, 564, 776; 433/201.1, 229

[56] References Cited

U.S. PATENT DOCUMENTS

| | | |
|---|---|---|
| 3,935,944 | 2/1976 | Wilson et al. ........................... 206/776 |
| 4,856,648 | 8/1989 | Krueger ................................. 206/63.5 |
| 4,976,351 | 12/1990 | Mangini .............................. 206/459.5 |
| 5,040,680 | 8/1991 | Wilson et al. ....................... 206/459.5 |
| 5,289,919 | 3/1994 | Fischer ................................. 206/63.5 |
| 5,558,230 | 9/1996 | Fischer et al. ........................ 206/63.5 |
| 5,622,500 | 4/1997 | Niznick ................................. 206/63.5 |

*Primary Examiner*—Jacob K. Ackun
*Assistant Examiner*—Luan K. Bui
*Attorney, Agent, or Firm*—Knobbe, Martens, Olson, & Bear LLP

[57] ABSTRACT

A dental implant prosthesis component package and display system for containing sterile dental prostheses and components thereof for convenient use by a dentist or oral surgeon is disclosed.

3 Claims, 1 Drawing Sheet

# 5,979,643

DENTAL IMPLANT PROSTHESIS COMPONENT DISPLAY SYSTEM

FIELD OF THE INVENTION

This invention relates to dental implant technology.

BACKGROUND OF THE INVENTION

Dental implant technology is very well developed and there is a large body of literature describing this technology in technical reports, professional literature and patents. Indeed, within the past decade, this has become a very crowded art.

The prior art discloses a vast array of dental implant prosthesis components. For convenience, the term "prosthetic components" or simply "components" will be used herein as a shorthand reference to all of the components of a dental restoration or other procedure that involves the implantation of a pin, screw or other device into the jaw of a patient, including the components attached thereto, such as abutments, copings, prostheses and attaching components such as screws, pins, washers, etc. The particular configuration described in detail hereinafter as exemplary is used for prosthetic implants and may be used for drills. The reader is referred to the following United States Patents to illustrate, in general, a few of the types of components that may be used: U.S. Pat. No. 5,476,382 to Daftary; U.S. Pat. No. 5,431,576 to Daftary; U.S. Pat. No. 5,030,096 to Hurson, et. al., and U.S. Pat. No. 4,856,648 to Krueger.

The components use in dental implant prosthesis technology are very small; so small, indeed, that in many instances it is impossible visually to distinguish between different sizes, and sometime even between different components. Magnification and/or the use of calipers or other measuring devices is often necessary to ascertain exactly the type and size of the component.

A great variety of types and sizes of components must be kept on hand to assure that the dentist or oral surgeon has the right type of component in the right size to treat a patient. Sometimes, a preliminary procedure or examination enables the doctor to determine in advance the type and size of dental implant prosthesis, abutment, coping, etc., that will be required; however, a change of type or size may be required while a procedure is being carried out as a result of the discovery of a problem not previously known, or some other circumstance which cannot be fully determined until the procedure begins. Often, of course, the type or size of a dental implant prosthesis component is unknown or cannot be determined until a dental or surgical procedure is begun. In all cases, however, it is important that the doctor have on hand a substantial number of components to assure that the proper components are on hand.

Prostheses and implant components, being very small, are difficult to handle. Many are so small that extremely well developed manual dexterity is required simply to hold them in a given position and special holding tools are required to use them.

Efforts to provide packaging and holders to enable the doctor to identify, select and/or to hold the component and to use the component in a dental or surgical procedure have met with limited success. U.S. Pat. No. 4,856,648 to Krueger, U.S. Pat. No. 5,290,171 to Daftary and U.S. Pat. No. 5,030,096 to Hurson, et. al., are exemplary of such efforts.

A companion problem is that of maintaining sterility of the dental implant prosthesis component. Such components are frequently pre-sterilized by the manufacturer in a sealed package or envelope. Sterility is reliably obtained and reasonably assured so long as the sterile package is not opened or damaged. The dentist often finds it difficult to handle these small components and yet maintain sterility. The component must be removed from the sterile package and transferred to the opening in the patient's mandible or maxilla directly or by way of a sterile surgical holder or instrument. Removing the small component from the package while maintaining sterility is a serious inconvenience. Facets of this problem, and examples of the types of components of concern, are addressed in the following U.S. Pat. Nos.: 4,976,617 to Carchidi; 4,941,227 to Sussman; 5,062,800 to Niznick; 5,290,171 to Daftary, et. al.,; 5,368,160 to Leuschen, et. al.; 5,538,428 to Staubli; 5,558,230 to Fischer, et. al.; and 5,582,299 to Lazzara et. al. One facet of the present invention addresses this problem.

Notwithstanding the many efforts in this crowded art to provide the doctor with dental implant prostheses and components thereof to permit quick and certain identification and provide means for handling prostheses and implant components, there remains the need for a compact orderly system and apparatus to minimized space requirements in the doctor's operating room and, at the same time, present the components in a convenient manner for identification, handling and use. This invention meets this need more efficiently and more conveniently that any system or apparatus of which the inventors are aware.

SUMMARY OF THE INVENTION

The present invention is embodied in a dental implant prosthesis component package and display system for containing sterile dental implant prostheses and components thereof for convenient use by a dentist or oral surgeon. The system comprises, in combination, a display box comprising a base and a transparent cover. The base comprises a frame defining a plurality of shallow receptacle compartments. The cover is formed entirely or in substantial part of transparent material and is constructed and configured to fit snugly over and extend above the base. The combined base and cover define an enclosure which is visible through the cover from outside the enclosure. A plurality of component packages constructed and configured to fit inside the enclosure in the receptacle compartments, each of which is visible and any of which can be selected independently nest inside the enclosure. A component of a dental implant prosthesis or dental prosthesis is contained inside the component package.

Indicia on the component packages encode information defining the size of the dental implant prosthesis or dental prosthesis or component and other indicia may depict the dental implant prosthesis or dental prosthesis or component in the package.

DESCRIPTION OF THE PREFERRED EMBODIMENTS

Figures 1, 2, 3:
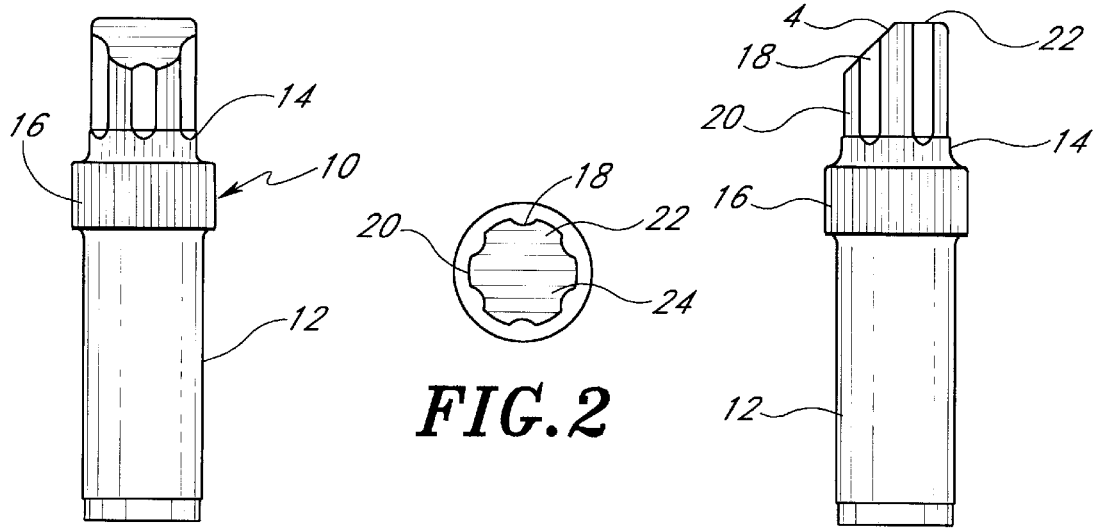
FIG. 1 is a front elevational view of a dental prosthetic component package of this invention.
FIG. 2 is a top view of the dental prosthetic component package shown in FIG. 1.
FIG. 3 is a side elevational view of the dental prosthetic component package of FIG. 1.

The following description and the exemplary embodiments depicted in the drawings disclose the best form of the invention presently known to the inventors. Neither the description nor the drawings are, however, limiting. There are many facets to the invention. The invention can be made of a combination of any of a large number of materials. The configuration of each of the individual components may vary considerably, so long as the relationship permits display and use. Indeed, many variations and adaptations can be made within the spirit of the invention and without departing from the claims. Thus, the specification and drawings are exemplary, not limiting.

The package 10 comprises a generally cylindrical container 12 and a cap 14. The container 12 is more or less conventional. It is desirably made of a transparent sterilizable plastic, e.g., polystyrene, polycarbonate, vinyl copolymer, etc., however, the material is not critical and any material that is sterilizable and sufficiently strong and light may be used.

The cap 14 is of a highly unique and functional configuration. The cap 14 has a flange 16 which may be threaded and screwed on the container 12 or it may be cylindrical for being snugly slip fitted over the top of container 12 to form, in either case, an air tight seal to maintain sterility in the container. The cap may be but need not be transparent, but it should be sterilizable and some degree of self-lubricity is desired. Materials such as polycarbonates and polyacetals are exemplary of the kinds of materials that my be used to form the cap 14.

The cap 14 is generally cylindrical in shape but has a plurality of elongate recesses 18 and grooved elongate protrusions 20 to enable the user to grip the cap. A very important feature of the cap is a two-plane top. The first plane 22 is generally perpendicular to the axis of the overall cylindrical configuration of the cap. The second plane 24 intersects and slopes from the first plane toward the bottom of the cap.

The cap structure provides two surfaces for providing two separate sets of identifying indicia, both visible but readily distinguishable, to be displayed on the top. As a part of the system of this invention, this is a very important feature.

The indicia are, of course, selected to identify the prosthesis component in the container and my vary according to need. In a preferred embodiment, indicia identifying the type of component is printed on the first plane and size and other specifications are printed on the second plane. Also in a preferred embodiment, the indicia are colored or printed on colored background to identify the prosthesis component as part of a particular size of prosthetic set. Red may identify one size, e.g., 5 mm, of prosthesis set, blue another, etc.

The printing may be directly on the cap structure such a by screen printing or the printing my be on a label applied to the two planes of the top of the cap.

Figure 4:
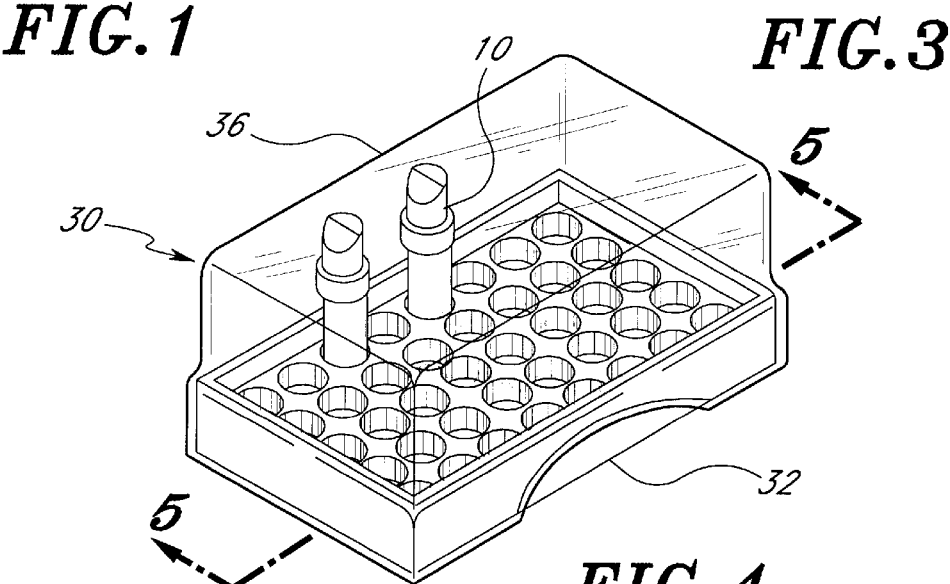
FIG. 4 is a perspective view of an implant prosthesis component display box which, in combination with the package shown in FIGS. 1–3, makes up the orderly system of packaging and holding dental prosthetic components. A plurality of such boxes can be nested one on top of the other, permitting the box of current interest to reside on top to display components of a predetermined size and/or type.
Figure 5:
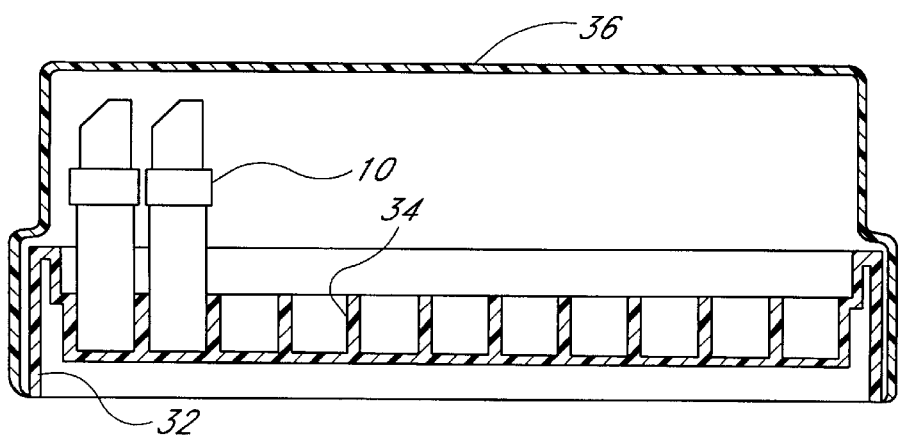
FIG. 5 is a cross-sectional view of the box of FIG. 1 taken along lines 5—5 as shown in FIG. 4.

As shown in FIGS. 4 and 5, the system of the invention also comprises a stackable display box 30 which comprises a base 32 that defines a plurality of recesses 34 constructed and configured to receive and position the bottom of the container 12 and a transparent or substantially transparent cover 36 that may comprise a cutaway portion 38 to enable the user to grasp the cover and the base for opening the box. The base, as clearly shown in FIG. 5, comprises the base comprising a peripheral frame defining a shallow receptacle compartment to receive a plurality of the previously described packages. The box is configured and constructed to hold and to position for display a plurality of the packages shown in FIGS. 1–3, two exemplary packages being shown in position for display in FIGS. 4 and 5. As ponted out, the cover is formed in substantial part of transparent material and as shown in FIG. 5 is constructed and configured to fit snugly over and extend above the base. The combined base and cover define an enclosure visible through the cover from outside the enclosure;

The box base may be made of any material, most polymeric materials, e.g., polystyrene, acrylic polymers, etc., are entirely satisfactory. The cover may, likewise, be made of any such material so long as at least the top portion of the cover is transparent. It may, in some manufacturing operations, be desirable to make the box of a sterilizable material such as polycarbonate, etc.; however, since each package is sterile, it is usually not necessary that the box be sterilizable.

As best shown in FIGS. 4 and 5 a plurality of component packages constructed and configured to fit inside the enclosure are positioned by the base to define at least one symmetrical column. Each of the packages comprises a cylindrical container and a cap defining an air-tight component containing space. A component of a dental implant prosthesis is contained inside the component package. Indicia on the component packages encoding information define the tyoe and size of the component contained therein.

Industrial Application

This invention is useful in the dental prosthesis industry and in dentistry and oral surgery.

What is claimed is:

1. A dental implant prosthesis component display system for containing sterile dental implant prostheses and components thereof for convenient use by a dentist or oral surgeon comprising, in combination:

a display box comprising a base and a transparent cover, the base comprising a peripheral frame defining a shallow receptacle compartment, the cover being formed in substantial part of transparent material and being constructed and configured to fit snugly over and extend above the base, the combined base and cover defining an enclosure visible through the cover from outside the enclosure, the base defining plural columns of generally cylindrical recesses for receiving receptacles;

a plurality of generally cylindrical component packages each having substantially the same cross-sectional configuration constructed and configured to fit snugly inside the enclosure in said recesses, each of said packages comprising a bottom, walls and a top defining component containing space;

a component of a dental implant prosthesis or dental prosthesis inside the packages;

indicia on the component packages encoding information defining the size of the component contained therein; and caps closing said packages, said caps defining a generally cylindrical structure having a cylindrical axis, ends for being received on said packages, generally cylindrical walls defining gripping structure configured and constructed to permit the user to grip the caps and a closed end, the closed end being configured and constructed to define two intersecting planar surfaces, one of said planar surfaces being substantially perpendicular to said axis, the other of said planer surfaces defining with said axis an angle of less than 90 degrees.

2. The system of claim 1 further comprising indicia on both of said planar surfaces to identify the type of component and other specifications.

3. The system of claim 2 wherein the indicia on at least one of said planar surfaces are printed on colored background to identify the prosthesis component as part of a particular size of prosthetic set.

\* \* \* \* \*